United States Patent [19]

Berthold et al.

[11] Patent Number: 5,347,050

[45] Date of Patent: Sep. 13, 1994

[54] 3-AMINOPROPOXYPHENYL DERIVATIVES, THEIR PREPARATION AND PHARMACEUTICAL COMPOSITIONS CONTAINING THEM

[76] Inventors: Richard Berthold, 9 Ahornstrasse, CH-4103 Bottmingen, Switzerland; William J. Louis, 3 Balmoral Avenue, Kew, 3101 Victoria, Australia

[21] Appl. No.: 46,937

[22] Filed: Apr. 13, 1993

Related U.S. Application Data

[60] Continuation of Ser. No. 782,791, Oct. 21, 1991, abandoned, which is a continuation of Ser. No. 584,306, Sep. 17, 1990, abandoned, which is a continuation of Ser. No. 474,185, Feb. 2, 1990, abandoned, which is a continuation of Ser. No. 399,721, Aug. 25, 1989, abandoned, which is a continuation of Ser. No. 307,028, Feb. 3, 1989, abandoned, which is a continuation of Ser. No. 173,845, Mar. 28, 1988, abandoned, which is a continuation of Ser. No. 897,557, Aug. 18, 1986, abandoned, which is a continuation of Ser. No. 778,831, Sep. 23, 1985, abandoned, which is a continuation of Ser. No. 567,471, Jan. 3, 1984, abandoned, which is a division of Ser. No. 318,292, Nov. 4, 1981, Pat. No. 4,425,362.

[30] Foreign Application Priority Data

| Nov. 6, 1980 [CH] | Switzerland | 8249/80 |
| Dec. 18, 1980 [CH] | Switzerland | 9347/80 |
| Jun. 19, 1981 [CH] | Switzerland | 4073/81 |
| Jun. 19, 1991 [CH] | Switzerland | 4074/81 |

[51] Int. Cl.$^5$ .......................... C07C 93/06
[52] U.S. Cl. ................ 564/349; 568/38; 568/39; 568/41; 568/44; 568/45; 568/51; 568/583; 568/584; 568/587; 568/592; 568/648
[58] Field of Search ............. 568/38, 43, 586, 648, 568/39, 41, 44, 45, 57, 583, 584, 887; 514/712, 716, 717, 718, 715; 564/349

[56] References Cited

U.S. PATENT DOCUMENTS 4,252,984  2/1981  Manaury et al. ............. 564/349

Primary Examiner—José G. Dees
Assistant Examiner—Deborah D. Carr
Attorney, Agent, or Firm—Sughrue, Mion, Zinn, Macpeak & Seas

[57] ABSTRACT

The compounds of formula I,

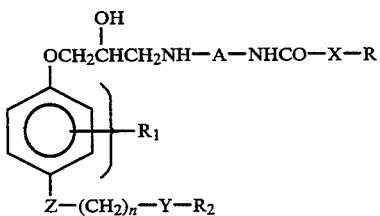

wherein the substituents have various significances, and physiologically acceptable hydrolyzable derivatives thereof having the hydroxy group in the 2 position of the 3-aminopropoxy side chain in esterified form, are useful as cardioselective β-adrenoceptor blocking agents.

7 Claims, No Drawings

3-AMINOPROPOXYPHENYL DERIVATIVES, THEIR PREPARATION AND PHARMACEUTICAL COMPOSITIONS CONTAINING THEM

This is a continuation of application No. 07/782,791 filed Oct. 21, 1991; now abandoned which is a continuation of application No. 07/584,306, filed Sep. 17, 1990, now abandoned; which is a continuation of application No. 07/474,185, filed Feb. 2, 1990, now abandoned; which is a continuation of application No. 07/399,721, filed Aug. 25, 1989, now abandoned; which is a continuation of application No. 07/307,028, filed Feb. 3, 1989, now abandoned; which is a continuation of application No. 07/173,845, filed Mar. 28, 1988, now abandoned; which is a continuation of application No. 06/897,557, filed Aug. 18, 1986, now abandoned; which is a continuation of application No. 06/778,831, filed Sep. 23, 1985, now abandoned; which is a continuation of application No. 06/567,471, filed Jan. 3, 1984, now abandoned; which is a divisional of application No. 06/318,292, filed Nov. 4, 1981, now U.S. Pat. No. 4,425,362.

The present invention relates to 3-aminopropoxyphenyl derivatives, their preparation and pharmaceutical compositions containing them.

In accordance with the invention there are provided compounds of formula I,

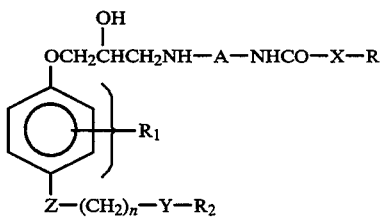

wherein

R is alkyl, alkenyl, cycloalkyl, cycloalkylalkyl or optionally substituted aryl, aralkyl or aralkenyl, $R_1$ is hydrogen or a substituent, $R_2$ is hydrogen or has the significance indicated above for R, A is alkylene, X is a bond or imino, Y is an oxygen or a sulfur atom and either Z is an oxygen atom and n is 2 or 3 or Z is a bond and n is 1, 2 or 3, with the proviso that when $R_2$ is cycloalkylalkyl, R is alkyl and X is a bond, then $R_1$ is other than hydrogen, and physiologically acceptable hydrolyzable derivatives thereof having the hydroxy group in the 2 position of the 3-aminopropoxy side chain in esterified form, hereinafter referred to as "the compounds of the invention".

"Alkylene" only comprises radicals having a carbon chain of at least 2 carbon atoms separating X from the nitrogen atom of the 3-aminopropoxy side chain.

In accordance with the invention, there are especially provided compounds of formula Ia,

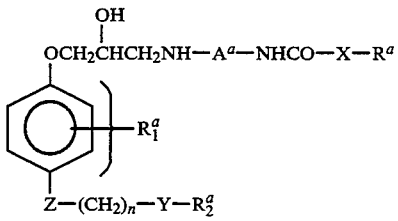

wherein X, Y, Z and n are as defined above and $R^a$ is alkyl of 1 to 4 carbon atoms, alkenyl of 3 to 5 carbon atoms wherein the double bond is not attached to the carbon atom adjacent to X, cycloalkyl of 5 to 7 carbon atoms, cycloalkylalkyl of 3 to 7 carbon atoms in the cycloalkyl moiety and of 1 to 4 carbon atoms in the alkyl moiety thereof, or phenyl, phenylalkyl of 7 to 10 carbon atoms or phenylalkenyl of 8 to 11 carbon atoms wherein the double bond is not attached to the carbon atom adjacent to X, the last three substituents optionally being i) monosubstituted in the phenyl ring by alkyl of 1 to 4 carbon atoms, alkoxy of 1 to 4 carbon atoms, halogen of atomic number of from 9 to 35, hydroxy, cyano, trifluoromethyl, hydroxymethyl, carbamoyl, alkoxyalkoxy of 1 to 4 carbon atoms in each of the alkoxy moieties thereof, amino or alkanoylamino of 1 to 5 carbon atoms, or ii) independently disubstituted in the phenyl ring by alkyl of 1 to 4 carbon atoms, hydroxymethyl, carbamoyl, cyano, alkoxy of 1 to 4 carbon atoms, halogen of atomic number of from 9 to 35 or hydroxy, or iii) independently trisubstituted in the phenyl ring by alkyl of 1 to 4 carbon atoms or alkoxy of 1 to 4 carbon atoms, $R_1{}^a$ is hydrogen, alkyl of 1 to 4 carbon atoms, alkoxy of 1 to 4 carbon atoms, alkylthio of 1 to 4 carbon atoms, cycloalkyl of 3 to 7 carbon atoms, halogen of atomic number of from 9 to 53, trifluoromethyl, pyrrol-1-yl, cyano, carbamoyl, alkenyl of 2 to 5 carbon atoms, alkenyloxy of 3 to 5 carbon atoms wherein the double bond is not attached to the carbon atom adjacent to the oxygen atom, alkanoyl of 2 to 5 carbon atoms, nitro, amino, alkanoylamino of 1 to 5 carbon atoms or alkoxycarbonylamino of 1 to 4 carbon atoms in the alkoxy moiety thereof, $R_2{}^a$ is hydrogen, alkyl of 1 to 5 carbon atoms, alkenyl of 3 to 5 carbon atoms wherein the double bond is not attached to the carbon atom adjacent to Y, cycloalkyl of 5 to 7 carbon atoms, cycloalkylalkyl of 3 to 7 carbon atones in the cycloalkyl moiety and of 1 to 4 carbon atoms in the alkyl moiety thereof, or phenyl, phenylalkyl of 7 to 10 carbon atoms or phenylalkenyl of 8 to 11 carbon atoms wherein the double bond is not attached to the carbon atom adjacent to Y, the last three substituents optionally being mono- or independently di- or independently trisubstituted in the phenyl ring by alkyl of 1 to 4 carbon atoms, alkoxy of 1 to 4 carbon atoms or halogen of atomic number of from 9 to 35 and $A^a$ is alkylene of 2 to 5 carbon atoms, with the proviso that when $R_1{}^a$ is cycloalkylalkyl, $R^a$ is alkyl and X is a bond, then $R_1^a$ is other than hydrogen,
and physiologically acceptable hydrolyzable derivatives thereof having the hydroxy group in the 2 position of the 3-aminopropoxy side chain in esterified form.

A physiologically hydrolyzable derivative is a derivative which under physiological conditions is split to the corresponding compound having a hydroxy group in the 2 position of the 3-aminopropoxy side chain.

A group of derivatives in esterified form of the compounds of formula I is e.g. the compounds of formula E,

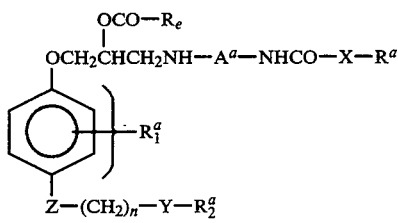

wherein
$R^a$, $R_1^a$, $R_2^a$, $A^a$, X, Y, Z and n are as defined above and $R_e$ is alkyl of 1 to 12 carbon atoms, cycloalkyl of 3 to 7 carbon atoms, phenyl, phenylalkyl of 7 to 12 carbon atoms, or phenyl or phenylalkyl of 7 to 12 carbon atoms monosubstituted in the phenyl ring by alkyl of 1 to 4 carbon atoms, or mono- or independently disubstituted in the phenyl ring by halogen of atomic number of from 9 to 35, or mono- or independently di- or independently trisubstituted in the phenyl ring by alkoxy of 1 to 4 carbon atoms.

Preferred are the compounds of the invention wherein the hydroxy group in the 2 position of the 3-aminopropoxy side chain is in unesterified form.

Any monosubstituted phenyl ring appearing in or as a substituent preferably is substituted in the para position. Any disubstituted phenyl ring preferably is substituted in the meta and para positions.

Any trisubstituted phenyl ring preferably is substituted in the meta, meta, para positions. Any phenyl ring preferably is unsubstituted, mono- or disubstituted. Any polysubstituted phenyl ring preferably is substituted by identical substituents, unless indicated otherwise hereunder. Any trisubstituted phenyl ring preferably is substituted by alkoxy.

Alkyl of 1 to 4 carbon atoms and/or alkoxy of 1 to 4 carbon atoms and/or alkylthio of 1 to 4 carbon atoms preferably are of 1 or 2 carbon atoms, especially of 1 carbon atom. Alkyl of 1 to 5 carbon atoms preferably is of 3 or 4 carbon atoms; it preferably is branched. Halogen of atomic number of from 9 to 35 or of from 9 to 53 preferably is chlorine or bromine, especially bromine. Cycloalkyl of 3 to 7 carbon atoms preferably is of 3, 5 or 6 carbon atoms, especially 5 or 6 carbon atoms. Cycloalkyl of 5 to 7 carbon atoms preferably is of 5 or 6 carbon atoms, especially of 6 carbon atoms. Alkenyl of 2 to 5 carbon atoms preferably is of 2 or 3 carbon atoms, it especially is allyl. Alkenyl of 3 to 5 carbon atoms preferably is of 3 carbon atoms; it especially is allyl. Alkenyloxy of 3 to 5 carbon atoms preferably is of 3 or 4 carbon atoms; it especially is allyloxy. Cycloalkylalkyl of 3 to 7 carbon atoms in the cycloalkyl moiety and of 1 to 4 carbon atoms in the alkyl moiety thereof is especially of 3, 5 or 6 carbon atoms in the cycloalkyl moiety and especially of 1 or 2 carbon atoms in the alkyl moiety thereof; it preferably is cyclopropylmethyl. Phenylalkyl of 7 to 10 carbon atoms preferably is of 7 or 8 carbon atoms; it especially is benzyl. Phenylalkenyl of 8 to 11 carbon atoms preferably is of 8 or 9 carbon atoms; it especially is cinnamyl. Alkoxyalkoxy of 1 to 4 carbon atoms in each of the alkoxy moieties thereof preferably has 1 or 2, especially 1 carbon atom in the terminal alkoxy moiety and preferably 2 carbon atoms in the other alkoxy moiety; it especially is methoxyethoxy. Alkanoylamino of 2 to 5 carbon atoms preferably is of 2 or 3 carbon atoms; it especially is acetamido. Alkanoyl of 1 to 5 carbon atoms preferably is of 2 or 3 carbon atoms; it especially is acetyl. Alkoxycarbonylamino of 1 to 4 carbon atoms in the alkoxy moiety thereof preferably is of 1 or 2 carbon atoms in the alkoxy moiety; it especially is methoxycarbonylamino. Alkylene of 2 to 5 carbon atoms preferably is ethylene. When it is of more than 2 carbon atoms, then it preferably is trimethylene or a moiety branched in the α position, such as

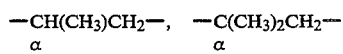

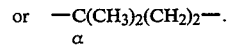

$R^a$ preferably is alkyl or optionally substituted phenyl or phenylalkyl, especially optionally substituted phenyl or phenylalkyl. When it is optionally substituted phenyl, phenylalkyl or phenylalkenyl, it preferably is unsubstituted or monosubstituted. When the phenyl ring is monosubstituted, it preferably is substituted by alkoxy, alkoxyalkoxy, carbamoyl, hydroxy or cyano, especially by alkoxy or hydroxy. When the phenyl ring is disubstituted, it preferably is disubstituted by alkoxy or by alkoxy and hydroxy.

$R_1^a$ preferably is in the position on the phenyl ring ortho to the 3-aminopropoxy side chain. It preferably is hydrogen, cycloalkyl, cyano, carbamoyl, halogen, alkenyl or alkenyloxy, especially hydrogen, cyano or halogen, especially cyano or halogen.

$R_2^a$ preferably is alkyl, cycloalkylalkyl or optionally substituted phenylalkyl, especially alkyl or cycloalkylalkyl, especially cycloalkylalkyl. When it is optionally substituted phenyl, phenylalkyl or phenylalkenyl, it preferably is unsubstituted or monosubstituted. When the phenyl ring is substituted, it preferably is substituted by alkoxy.

X preferably is imino.
Y preferably is an oxygen atom.
Z preferably is an oxygen atom.
n preferably is 2.

A preferred group of compounds of the invention is the compounds of formula Iaa,

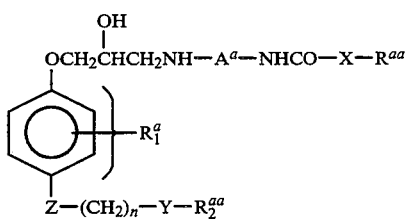

wherein $R_1^a$, $A^a$, X, Y, Z and n are as defined above,
$R^{aa}$ with the exceptions of alkyl and substituted or unsubstituted phenylalkyl has the significance indicated above for $R^a$ and $R_2^{aa}$ is hydrogen, alkyl of 1 to 4 carbon atoms, alkenyl of 3 to 5 carbon atoms wherein the double bond is not attached to the carbon atom adjacent to Y, cycloalkyl of 5 to 7 carbon atoms or cycloalkylalkyl of 3 to 7 carbon atoms in the cycloalkyl moiety and of 1 to 4 carbon atoms in the alkyl moiety thereof, and physiologically acceptable hydrolyzable derivatives thereof having the hydroxy group in the 2 position of the 3-aminopropoxy side chain in esterified form.

Another preferred group of compounds of the Invention is the compounds of formula Iaaa,

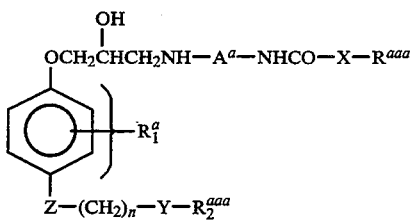

Iaaa wherein $R_1^a$, $A^a$, X, Y, Z and n are as defined above, $R^{aaa}$ is alkenyl of 3 to 5 carbon atoms wherein the double bond is not attached to the carbon atom adjacent to X, cycloalkyl of 5 to 7 carbon atoms, cycloalkylalkyl of 5 to 7 carbon atoms in the cycloalkyl moiety and of 1 to 4 carbon atoms in the alkyl moiety thereof or phenyl optionally monosubstituted by alkyl of 1 to 4 carbon atoms, alkoxy of 1 to 4 carbon atoms, halogen of atomic nun%her of from 9 to 35, hydroxy, cyano, trifluoromethyl hydroxymethyl, carbamoyl, alkoxyalkoxy of 1 to 4 carbon atoms in each of the alkoxy moieties thereof, amino or alkanoylamino of 1 to 5 carbon atoms, or independently disubstituted by alkyl of 1 to 4 carbon atoms, hydroxymethyl, carbamoyl, cyano, alkoxy of 1 to 4 carbon atoms, halogen of atomic number of from 9 to 35 or hydroxy, or independently trisubstituted by alkyl of 1 to 4 carbon atoms or alkoxy of 1 to 4 carbon atoms and $R_2^{aa}$ is alkyl of 1 to 4 carbon atoms or alkenyl of 3 to 5 carbon atoms wherein the double bond is not attached to the carbon atoms adjacent to Y, and physiologically acceptable hydrolyzable derivatives thereof having the hydroxy group in the 2 position of the 3-aminopropoxy side chain in esterified form.

In a subgroup of compounds of formula Iaaa $R^{aaa}$ is phenyl optionally substituted as indicated above. In another subgroup $R_2^{aaa}$ is alkyl of 1 to 4 carbon atoms. In another sub group $R_1^a$ is other than hydrogen. In another subgroup $R_1^a$ is in the position on the phenyl ring ortho to the 3-aminopropoxy side chain. In a further subgroup $R^{aaa}$ is phenyl optionally substituted as indicated above, $R_2^{aaa}$ is alkyl of 1 to 4 carbon atoms, $R_1^a$ is other than hydrogen and $R_1^a$ is in the position on the phenyl ring ortho to the 3-aminopropoxy side chain.

Another group of compounds of the invention is the compounds of formula Ias,

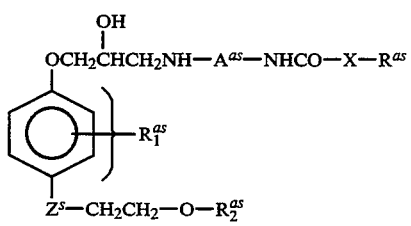

Ias wherein X is as defined above, $R^{as}$ is alkyl of 1 to 4 carbon atoms, cycloalkyl of 5 or 6 carbon atoms, or phenyl or phenylalkyl of 7 to 9 carbon atoms, the last two substituents optionally being
i) monosubstituted in the phenyl ring by alkyl of 1 or 2 carbon atoms, alkoxy of 1 or 2 carbon atoms, hydroxy, cyano, trifluoromethyl, hydroxymethyl, carbamoyl, alkoxymethoxy of 1 or 2 carbon atoms in the alkoxy moiety thereof or amino or
ii) independently disubstituted in the phenyl ring by alkyl of 1 or 2 carbon atoms, hydroxymethyl, carbamoyl, cyano, alkoxy of 1 or 2 carbon atoms or hydroxy, $R^{as}_1$ is hydrogen, halogen of atomic number of from 9 to 35, pyrrol-1-yl, cyano, carbamoyl, allyl, acetyl, acetamido or methoxycarbonylamino, $R_2^{as}$ is alkyl of 1 or 2 carbon atoms, cyclopropylmethyl or phenyl, $A^{as}$ is ethylene and $Z^s$ is a bond or an oxygen atom, with the proviso that, when $R_2^{as}$ is cyclopropylmethyl, $R^{as}$ is alkyl and X is a bond, then $R_1$ is other than hydrogen, and physiologically acceptable hydrolyzable derivatives thereof having the hydroxy group in the 2 position of the 3-aminopropoxy side chain in esterified form.

In a subgroup of compounds of formula $R_1^{as}$ is other than hydrogen. In another subgroup $R_1^{as}$ is in the position on the phenyl ring ortho to the 3-aminopropoxy side chain.

Another group of compounds of the invention is the compounds of formula Ipa,

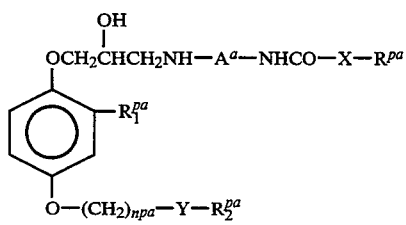

Ipa wherein $A^a$, X and Y are as defined above, $R^{pa}$ is phenyl unsubstituted or mono- or independently di- or independently trisubstituted by alkoxy of 1 to 4 carbon atoms, $R_1^{pa}$ is cyano, carbamoyl or pyrrol-1-yl, $R_2^{pa}$ is alkyl of 1 to 4 carbon atoms or cycloalkylalkyl of 3 to 7 carbon atoms in the cycloalkyl moiety and of 1 to 4 carbon atoms in the alkyl moiety thereof and $n^{pa}$ is 2 or 3.

Another group of compounds of the invention is the compounds of formula Ipb,

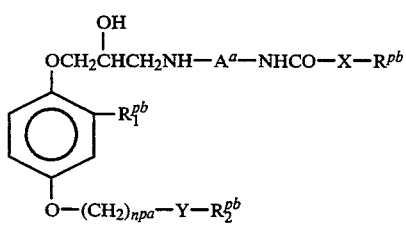

Ipb wherein $A^a$, X, Y and $n^{pa}$ are as defined above, $R^{pb}$ is phenyl unsubstituted or mono- or independently di- or independently trisubstituted by alkyl of 1 to 4 carbon atoms or alkoxy of 1 to 4 carbon atoms, $R_1^{pb}$ is hydrogen, alkyl of 1 to 4 carbon atoms, alkoxy of 1 to 4 carbon atoms, cycloalkyl of 3 to 7 carbon atoms, halogen of atomic number of from 9 to 53, alkenyl of 3 to 5 carbon atoms wherein the double bond is not attached to the carbon atom adjacent to the phenyl ring, alkenyloxy of 3 to 5 carbon atoms wherein the double bond is not attached to the carbon atom adjacent to the oxygen atom or alkanoylamino of 2 to 5 carbon atoms and $R_2^{pb}$ is alkyl of 1 to 4 carbon atoms or cycloalkylalkyl of 3 to 7 carbon atoms in the cycloalkyl moiety and of 1 to 4 carbon atoms in the alkyl moiety thereof.

In accordance with the invention, a compound of the invention may be obtained by a process which includes the step of appropriately 3-amino-2-oxypropylating a corresponding compound of formula IV,

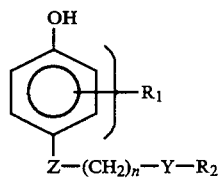   IV wherein $R_1$, $R_2$, Z, Y and n are as defined above, or a precursor form thereof.

The process step of the invention may be effected in conventional manner for the production of analogous 3-amino-2-oxy-propoxyaryl compounds.

The choice of the most appropriate variant should, of course, take into account the reactivities of the substituents present.

Preferably a compound of formula IV is used, rather than a precursor form thereof.

A precursor form of a compound of formula IV is a compound capable of being converted into a compound of formula IV, e.g. by appropriate etherification, or by deprotection. Thus, when Z is oxygen, a precursor form is e.g. a corresponding compound wherein the moiety —O—$(CH_2)_{2,3}$—Y—$R_2$ is replaced by a hydroxy group, optionally in protected form. For those compounds wherein $R_2$ is other than hydrogen, a precursor form is e.g. a corresponding compound wherein the moiety —Y—$R_2$ is hydroxy or sulfhydryl, optionally in protected form. For those compounds wherein $R_2$ is hydrogen, a precursor form is e.g. a compound wherein the moiety —Y—H is in protected form.

Thus, this process step of the invention may be effected in more than one stage. For example, a compound of formula IV in protected form may be used, or a 3-amino-3-oxypropyl moiety in protected form may be introduced, and subsequently, after the 3-amino-2-oxypropylation has been effected, any protecting group present may be split off.

Benzyl, methyl or tetrahydropyranyl, preferably benzyl, are examples of a protecting group for e.g. a hydroxy-substituted phenyl ring.

In one form of the process according to the invention, the 3-amino-2-oxypropylation is effected in two main stages.

In a first stage, a group —$CH_2$—$R_x$, wherein $R_x$ is a group capable of reacting with a primary amine to give a 2-amino-1-hydroxyethyl group, is introduced by O-alkylation into a compound of formula IV to give a corresponding compound of formula II,

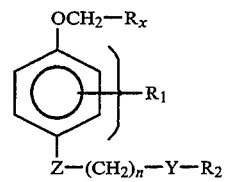   II wherein $R_x$, Z, Y, n, $R_1$ and $R_2$ are as defined above.

In a second stage, a compound of formula II is reacted with a corresponding compound of formula III, $$H_2N—A—NHCO—X—R \qquad III$$

wherein A, X and R are as defined above, and, where required, the 2 position of the 3-aminopropoxy side chain in a resultant compound of formula I is appropriately esterified.

The O-alkylation stage may be effected in a manner known for the production of analogous ethers. A compound of formula IV preferably is reacted in anionic form.

The amination process stage may be effected in conventional manner for the production of analogous 3-amino-2-hydroxypropoxyaryl compounds. For example, $R_x$ may be a group of formula)

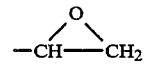

or a derivative of this group, e.g. a group of formula —CH(OH)—$CH_2$L, wherein L is chlorine, bromine or a group $R_y$—$SO_2$—O—, wherein $R_y$ is phenyl tolyl or lower alkyl. L is especially chlorine. The reaction is preferably effected in ethanol or in an appropriate ether such as dioxane. Optionally an excess of the amine may be used as solvent. Alternatively, the reaction may be effected in a fusion melt. Suitable reaction temperatures may be from about 20° to about 200° C., conveniently the reflux temperature of the reaction mixture when a solvent is present.

The optional esterification of the 2 hydroxy group in the 3-aminopropoxy side chain may be effected in manner known for the production of analogous esters of 3-amino-2-hydroxypropoxyaryl compounds, if necessary using selective reactions when other reactive groups, e.g. hydroxy or amino, are present.

The compounds of the invention may exist free form, i.e. normally as a base, or in salt form. Free forms of the compounds of the invention may be converted into salt forms, e.g. acid addition salt forms, and vice versa, in conventional manner. Suitable acids for acid addition salt formation include hydrochloric, malonic and fumaric acid.

In the compounds of the invention, the carbon atom in e.g. the 2 position of the 3-aminopropoxy side chain is asymmetrtcally substituted. The compounds may thus exist in the racemic form or in individual optical isomer form. The preferred optical isomer has the S-configuration at this asymmetrically substituted carbon atom of the 3-aminopropoxy side chain. Individual optical isomer forms may be obtained in conventional manner, for example by using optically active starting materials or by fractional crystallisation of racemate salts using optically active acids.

A compound used as a starting material may be obtained in conventional manner.

A compound of formula IIIa,

    IIIa wherein $A^a$ and $R^a$ are as defined above, may e.g. be obtained by reacting a corresponding compound of formula V

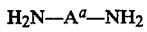    V wherein $A^a$ is as defined above, with a corresponding compound of formula VI,

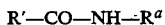    VI wherein $R^a$ is as defined above and R' is the functional residue of a carboxylic acid derivative.

A compound of formula VI may e.g. be obtained by reacting a corresponding compound of formula VII,

    VII wherein $R^a$ is as defined above, with a compound of formula VIII,

    VIII wherein R' is as defined above and R'' is also the functional residue of a carboxylic acid derivative.

Thus, a compound of formula VIII is a bifunctional carboxylic acid derivative, e.g. phosgene, carbonyldiimidazol or an ester of a carboxylic acid, e.g. carbonic acid diethyl ester, carbonic acid phenyl ethyl ester, carbonic acid diphenylester or chloroformic acid phenylester. The residues R' and R'' preferably are different.

A compound of formula IIIb,

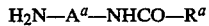    IIIb wherein $A^a$ and $R^a$ are as defined above, may e.g. be obtained by reacting a corresponding compound of formula V with a corresponding compound of formula IX,

    IX wherein $R^a$ is as defined above and R''' is the functional residue of an alcohol, e.g. ethyl orphenyl.

A compound of formula IX may e.g. be obtained by appropriately esterifying a compound of formula X,

    X wherein R''' is as defined above, with a corresponding compound of formula XI,
    XI wherein $R^a$ is as defined above, or a reactive derivative thereof, such as the acyl chloride or anhydride.

When in the compounds of formula IIIa or IIIb potentially sensitive groups such as hydroxy or amino on a phenyl ring, are present, it may be indicated to effect the above reactions with these groups in protected form. e.g. for hydroxy in the form of a benzyloxy moiety or for amino in the form of an acetamido moiety, and to subsequently split off any such protecting group to obtain the corresponding compound of formula III.

A compound of formula IVa,

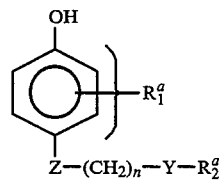    IVa wherein Y, Z, n, $R_1^a$ and $R_2^a$ are as described above, may e.g. be obtained by one or more of the following methods (when a product described hereunder has the hydroxy group in the position para to Z in protected form, a corresponding compound of formula IVa may be obtained after deprotection according to standard methods, e.g. with palladium on charcoal or by acidic hydrolysis):

A) Preparation of a compound of formula IVa, wherein Z is an oxygen atom

AA compound of formula XII,

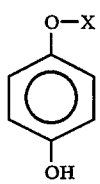    XII wherein X is a protecting group, e.g. benzyl, methyl or tetrahydropyranyl, preferably benzyl, may be appropriately etherified at the hydroxy moiety, e.g. by reaction with a molar equivalent of a compound of formula Hal—$(CH_2)_{n'}$—Y—$R_2$, wherein $R_2$, Y and n' are as defined above and Hal is halogen, preferably in an inert solvent such as acetone and in the presence of a base such as potassium carbonate, and the resultant ether may subsequently be deprotected to give a compound of formula IVaa,

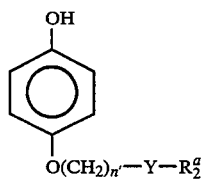    IVaa wherein $R_2^a$ and Y are as defined above and n' is 2 or 3.

A compound of formula IVaa may be monochlorinated, -brominated or -todinated to give a corresponding compound of formula IVa having a chlorine, bromine or iodine atom in the position ortho to the hydroxy group.

A compound of formula IVaa may also be appropriately etherified at the hydroxy moiety to give a corresponding compound with β, γ-alkenyloxy of 3 to 5 carbon atoms or cycloalkenyloxy of 5 or 6 carbon atoms and the resultant ether subjected to a Claisen rearrangement to form the corresponding ortho substituted phenol which is subsequently, when ortho-substituted by cycloalkenyl, hydrogenated. A compound of formula IVa wherein $R_1^a$ is β, γ-alkenyl of 3 to 5 carbon atoms or cycloalkyl of 5 or 6 carbon atoms, in the position ortho to the hydroxy moiety is obtained.

A compound of formula IVaa may also be subjected to a Friedel-Crafts acylation with an appropriate acyl chloride or to nitration to give a corresponding compound of formula IVa, wherein $R_1^a$ is alkanoyl of 2 to 5 carbon atoms or nitro, in the position ortho to the hydroxy group.

AB) A compound of formula XII may be monochlorinated, -brominated or -iodinated to give a corresponding compound having a chlorine, bromine or iodine atom in the position ortho to the hydroxy group. In the resultant compound the hydroxy moiety may be appropriately etherified and the resultant ether may be deprotected under mild conditions to give a corresponding hydroxy compound of formula IVa wherein $R_1^a$ is chlorine, bromine or iodine, in the position meta to the hydroxy group.

AC) A compound of formula XII may be subjected to Friedel-Crafts acylation with an appropriate acyl chloride or to nitration to give a corresponding compound having an alkanoyl moiety of 2 to 5 carbon atoms —or a nitro moiety in the position ortho to the hydroxy group. In the resultant compound the hydroxy group may be appropriately etherified, and the resultant compound may be deprotected to yield a corresponding compound of formula IVa, wherein $R_1^a$ is alkanoyl of 2 to 5 carbon atoms or nitro, in the position meta to the hydroxy group.

AD) A compound of formula IVab,

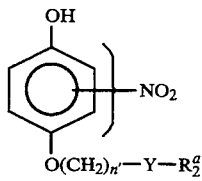

IVab wherein
n', Y and $R_2^a$ are as defined above (obtained e.g. according to AA) or AC) above), may e.g. be reduced according to Bechamps to give a corresponding compound of formula IVac,

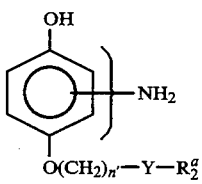

IVac wherein n', Y and $R_2^a$ are as defined above. A compound of formula IVac may be appropriately acylated to give a corresponding compound of formula IVa wherein $R_1^a$ is alkanoylamino of 1 to 5 carbon atoms. A compound of formula IVac may also be reacted with a corresponding chloroformic acid alkyl ester to give a corresponding compound of formula IVa wherein $R_1^a$ is alkoxycarbonylamino of 1 to 4 carbon atoms in the alkoxy moiety thereof.

AE) In a compound of formula IVad,

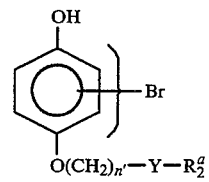

IVad wherein n', Y and $R_2^a$ are as defined above (prepared e.g. according to AA) or AB) above) the hydroxy moiety may be appropriately protected to give a compound of formula XIII,

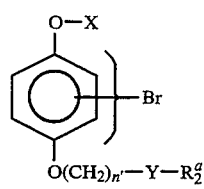

XIII wherein X, n', Y and $R_2^a$ are as defined above, and subsequently a compound of formula XIII may be converted in a Grignard-type reaction, e.g. with lithium, to a corresponding compound wherein bromine is replaced by alkyl of 1 to 4 carbon atoms, cycloalkyl of 3 to 7 carbon atoms or alkenyl of 2 to 5 carbon atoms. Alternatively, a compound of formula XIII may be converted to a corresponding-cyano compound, e.g. with cuprous cyanide in dimethyl formamide and subsequently, if desired, the cyano group may be hydrolysed to a carboxyl group and subsequently the carboxyl group converted to a trifluoromethyl group, e.g. by fluorination. Alternatively, a cyano compound may be hydrolyzed to a corresponding compound wherein the cyano group is replaced by carbamoyl. Subsequently, if desired, this carbamoyl compound may be converted in a Hofman type degradation into a corresponding amino derivative and this amino derivative converted e.g. with 2,5-dimethoxyfurane to a corresponding compound, wherein the amino group is replaced by pyrrol-1-yl. Alternatively, if desired, the amino derivative may be converted into a corresponding diazonium salt, e.g. with nitrous acid, and this diazonium salt further reacted with e.g. potassium fluoride in water to a corresponding compound, wherein the azo group is replaced by fluorine, or with e.g. an alkali metal mercaptide to a corresponding compound, wherein the azo group is replaced by alkylthio of 1 to 4 carbon atoms. Alternatively, the diazonium salt may be converted by reaction with aqueous acid to a corresponding hydroxy compound and this hydroxy compound converted by etherification into a corresponding compound wherein the hydroxy group is replaced by alkoxy of 1 to 4 carbon atoms or alkenyloxy of 3 to 5 carbon atoms wherein the double bond is not attached to the carbon atom adjacent to the oxygen atom.

B) preparation of a compound of formula IVa, wherein Z is a bond

BA) A compound of formula XIV,

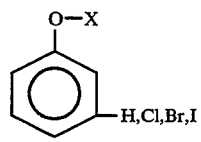

wherein X is as defined above (prepared e.g. by appropriately protecting a corresponding phenol) may e.g. be subjected to a Friedel-Crafts acylation with a corresponding compound of formula Hal—$(CH_2)_{1,2}$—Hal', wherein Hal and Hal' are halogen of atomic number of from 17 to 53, preferably bromine, and the resulting acyl compound may be reduced to a corresponding compound of formula XV,

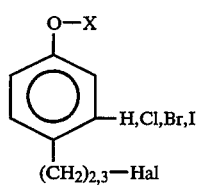

wherein X and Hal are as defined above.

A compound of formula XV may be reacted with the alkali metal salt of benzyl alcohol or benzyl mercaptan and the resultant benzyl ether or -thioether deprotected and subjected to ether or thioether splitting to give a corresponding compound of formula IVba,

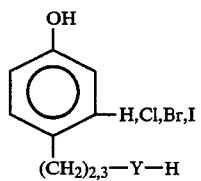

wherein Y is as defined above.

BB) A compound of formula XIV may be subjected to haloformylation to give a corresponding compound of formula XVI,

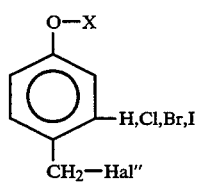

wherein X is as defined above, and Hal" is chlorine or bromine.

A compound of formula XVI may be deprotected to a corresponding hydroxy compound and the resultant hydroxy compound reacted with an alkali metal salt of thiourea to give a corresponding compound with a thioureidomethyl moiety in the position meta to the hydroxy group. The thioureidomethyl compound may subsequently be hydrolysed with mild alkali, e.g. ammonia, to give a corresponding compound of formula IVbb,

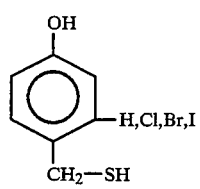

BC) A compound of formula XVI may also be hydrolyzed with e.g. sodium hydroxide solution to a corresponding compound of formula XVII,

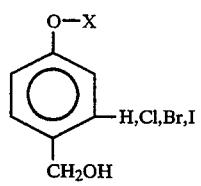

wherein X is as defined above.

BD) A compound of formula XV or XVI may also be appropriately etherified or thioetherified and the resultant ether or thioether deprotected to give: a compound of formula IVbc,

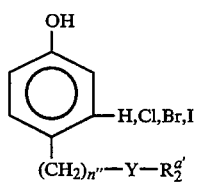

wherein Y is as defined above, n" is 1, 2 or 3 and $R_2^{a'}$ with the exception of hydrogen has the significance indicated above for $R_2^a$.

BE) A compound of formula IVba, IVbb or IVbc, wherein the position meta to the hydroxy group is unsubstituted, may be mono-chlorinated, -brominated or -iodinated in a position ortho to the hydroxy group to give a corresponding compound of formula IVbd,

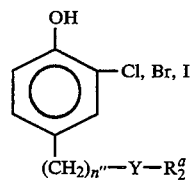

wherein n", $R_2^a$ and Y are as defined above.

BF) In a compound of formula XVIII,

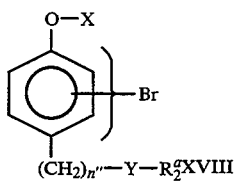

wherein n", X, Y and $R_2^a$ are as defined above (prepared e.g. according to BA) to BE) above, with where appropriate subsequent protection of the hydroxy group), the bromine moiety may be further reacted as described under AE) above for the compounds of formula XIII, to give a corresponding compound wherein the bromine moiety is replaced by alkyl of 1 to 4 carbon atoms, cycloalkyl of 3 to 7 carbon atoms, alkenyl of 2 to 5 carbon atoms, cyano, trifluoromethyl, carbamoyl, amino, pyrrol-1-yl, fluorine, alkylthio of 1 to 4 carbon atoms, alkoxy of 1 to 4 carbon atoms or alkenyloxy of 3 to 5 carbon atoms wherein the double bond is not attached to the carbon atoms adjacent to the oxygen atom.

BG) A compound of formula IVbe,

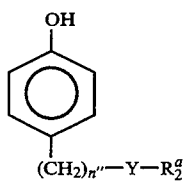

IVbe wherein n″, Y and R$_2^a$ are as defined above (prepared according to BA) to BE) above) may be subjected to a Friedel-Crafts acylation with an appropriate acyl chloride or to nitration to give a corresponding compound having an alkanoyl moiety of 2 to 5 carbon atoms or a nitro moiety in the position ortho to the hydroxy group.

BH) A compound of formula IVbf,

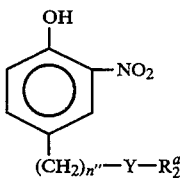

IVbf wherein R$_2^a$, Y and n″ are as defined above, may e.g. be reduced according to Bechamps to a corresponding amino compound and the resultant amino compound, if required, appropriately acylated to give a corresponding compound of formula IVa, wherein R$_1^a$ is alkanoylamino of 1 to 5 carbon atoms in the position ortho to the hydroxy group. The amino compound may also be reacted with a corresponding chloroformic acid alkyl ester to give a corresponding compound of formula IVa wherein R$_1^a$ is alkoxycarbonylamino of 1 to 4 carbon atoms in the alkoxy moiety thereof, in the position ortho to the hydroxy group.

BI) A compound of formula IVbg,

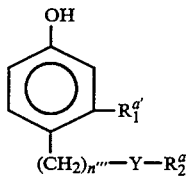

IVbg wherein R$_2^a$ and Y are as defined above, n‴ is 2 or 3, and R$_1^{a'}$ is alkanoyl of 2 to 5 carbon atoms, nitro, amino, alkanoylamino of 1 to 5 carbon atoms or alkoxycarbonylamino of 1 to 4 carbon atoms in the alkoxy moiety thereof, may e.g. be obtained by subjecting a compound of formula XIX,

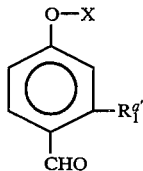

XIX wherein X and R$_1^{a'}$ are as defined above, to a Wittig reaction with a compound of formula XX,

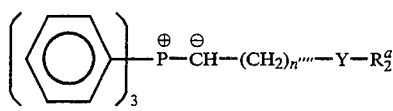

XX wherein R$_2^a$ and Y are as defined above and n″″ is 0 or 1 and subsequently catalytically hydrogenating, and deprotecting, a resultant compound of formula XXI

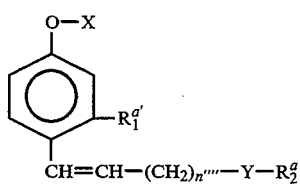

XXI wherein X, R$_1^{a'}$, R$_2^a$, n″″ and Y are as defined above.

BJ) A compound of formula IVbh

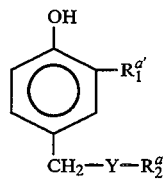

IVbh wherein R$_1^{a'}$, R$_2^a$ and Y are as defined above, may e.g. be obtained by reducing a corresponding compound having a formyl or thioformyl moiety in the position para to the hydroxy group, subsequently, if desired, appropriately etherifying the resultant compound, with subsequent deprotection.

Insofar as the preparation of any particular starting material is not particularly described, this may be effected in conventional manner.

In the following Examples all temperatures are in degrees Centigrade and are uncorrected.

Example 1: 1-[2-Cyano-4-(2-cyclopropylmethoxyethoxy)phenoxy]-3-[2-(3-phenylureido)ethylamino]2-propanol 1.2 g of 5-(2-Cyclopropylmethoxyethoxy)-2-2,3-epoxypropoxy)-benzonitrile and 1.47 g of 1-(2-aminoethyl)-3-phenylurea are melted together at 130° and heated at that temperature for a further 15 minutes. The fusion melt is then dissolved in dioxane, filtered over talc and the solvent evaporated to dryness. The residue is chromatographed on silicagel with methylene chloride/methanol/ammonia 100:40:5.7. After evaporation of the solvent of fractions 4 to 7 containing the title compound the oily residue is crystallized from methanol and ether. The title compound is obtained (M.P. 110°–113°).

The starting material is obtained as follows:

4-Benzyloxyphenel is reacted with 2-chloroethyl)cyclopropylmethyl)ether and the resultant 1-benzyloxy-4-(2-cyclopropylmethoxyethoxy)benzene is debenzylated by hydrogenation with palladium on charcoal. To a solution of the resultant 4-(2-cyclopropylmethoxyethoxy)phenol in methanol is added bromine dissolved in chloroform at 0° and the mixture stirred for 2 hours. After chromatography over silicagel, the resultant 2-bromo-4-(2-cyclopropylmethoxyethoxy)-phenol is reacted for 60 hours with a mixture of potassium carbonate, acetone and benzyl bromide. After chromatography over silicagel, the resultant 1-benzyloxy-2-bromo-4-(2-cyclopropylmethoxyethoxy)benzene is reacted in dimethylformamide for 5 hours with cuprous cyanide. After purification by partition between aqueous hydrochloric acid solution and ethyl acetate, the resultant 2-benzyloxy-5-(2-cyclopropylmethoxyethoxy)benzonitrile is debenzylat-d over 10 % palladium on charcoal in methanol. The resultant 2-hydroxy-5-(2-cyclopropylmethoxyethoxy)benzonitrile is reacted at 100° with epichlorhydrin and a catalytic amount of piperidine, and 2-(2,3-epoxypropoxy)-5-(2-cyclopropylmethoxyethoxy)benzonitrile is obtained.

From the appropriate compounds of formula II, wherein $R_x$ is

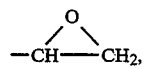

and the appropriate compounds of formula III the following compounds of formula I may be obtained in analogous manner to Example 1:

| Example No. | A | X | R | $R_1{}^{a)}$ | $R_2$ | Y | Z | n | | M.P. |
|---|---|---|---|---|---|---|---|---|---|---|
| 2 | ethylene | —NH— | phenyl | o-CN | methyl | O | O | 2 | hmo | 94–96° <br> 131–133° |
| 3 | ethylene | —NH— | phenyl | o-CN | cyclopropylmethyl | O | bond | 2 | b | 104–106° |
| 4 | ethylene | bond | p-OH-benzyl | o-CN | methyl | O | O | 2 | b | 113–116° |
| 5 | ethylene | bond | p-OH-benzyl | o-Br | methyl | O | O | 2 | hml | 136–137,5° |
| 6 | ethylene | —NH— | phenyl | o-Br | methyl | O | O | 2 | hmo <br> b | 142–144° <br> 130–132° |
| 7 | ethylene | —NH— | p-OH-phenyl | o-Br | methyl | O | O | 2 | b | 144–147° |
| 8 | ethylene | —NH— | p-OH-phenyl | o-CN | methyl | O | O | 2 | b | 126–129° |
| 9 | ethylene | —NH— | p-(2-methoxy-ethoxy)phenyl | o-Br | methyl | O | O | 2 | b | 143–145° |
| 10[b)] | ethylene | —NH— | phenyl | o-CONH$_2$ | methyl | O | O | 2 | b | 104–106° |
| 11[c)] | ethylene | —NH— | phenyl | O—N (ring) | methyl | O | O | 2 | b | 115–117° |
| 12 | ethylene | —NH— | p-MeO-phenyl | o-CN | methyl | O | O | 2 | b | 146–148° |
| 13 | trimethylene | —NH— | phenyl | o-CN | methyl | O | O | 2 | b | 126–128° |
| 14 | ethylene | —NH— | phenyl | H | methyl | O | O | 2 | b | 121–123° |
| 15 | ethylene | bond | phenyl | o-Br | methyl | O | O | 2 | b | 100–102° |
| 16 | ethylene | —NH— | phenyl | o-Cl | methyl | O | O | 2 | b | 135–136° |
| 17 | ethylene | —NH— | phenyl | o-Br | cyclopropylmethyl | O | O | 2 | b | 121–122° |
| 18 | ethylene | —NH— | phenyl | o-allyl | methyl | O | O | 2 | hmo | 114–115° |
| 19 | ethylene | —NH— | p-MeO-phenyl | o-Br | methyl | O | O | 2 | b | 158–160° |
| 20 | trimethylene | —NH— | phenyl | o-Br | methyl | O | O | 2 | b | 139–141° |
| 21[e)] | ethylene | —NH— | phenyl | o-NHCOMe | methyl | O | O | 2 | b | 110–112° |
| 22 | ethylene | —NH— | phenyl | H | p-MeO-benzyl | O | O | 2 | b | 123–125° |
| 23 | ethylene | bond | benzyl | o-Br | methyl | O | O | 2 | b | 99–104° |
| 24 | ethylene | —NH— | phenyl | H | cyclopropylmethyl | O | bond | 2 | b | 129–131° |
| 25 | ethylene | —NH— | phenyl | o-Br | cyclopropylmethyl | O | bond | 2 | b | 107–109° |
| 26 | ethylene | bond | isopropyl | o-Br | methyl | O | O | 2 | b | 114–117° |
| 27 | ethylene | bond | isopropyl | o-CN | methyl | O | O | 2 | b | 117–118.5° |
| 28 | ethylene | —NH— | tert-butyl | o-Br | methyl | O | O | 2 | b | 68–70° |
| 29 | ethylene | —NH— | n-butyl | o-Br | methyl | O | O | 2 | b | 115–117° |
| 30 | ethylene | —NH— | methyl | o-Br | methyl | O | O | 2 | b | 134–137° |
| 31 | ethylene | bond | benzyl | o-CN | methyl | O | O | 2 | b | 110–113° |
| 32[f)] | ethylene | —NH— | phenyl | o-NHCOOMe | methyl | O | O | 2 | ox | 176–178° |
| 33[g)] | ethylene | —NH— | phenyl | m-CN | methyl | O | O | 2 | b | 132–134° |
| 34[h)] | ethylene | —NH— | phenyl | m-NHCOMe | methyl | O | O | 2 | b | 87–91° |
| 35[i)] | ethylene | —NH— | phenyl | o-COMe | methyl | O | O | 2 | b | 113–116° |
| 36 | ethylene | —NH— | phenyl | m-Br | methyl | O | O | 2 | b | 132–133° |
| 37 | ethylene | —NH— | p-(2-methoxy-ethoxy)phenyl | o-CN | methyl | O | O | 2 | b | 155–157° |
| 38 | ethylene | —NH— | phenyl | H | cyclopropylmethyl | O | O | 2 | b | 122–124° |
| 39 | ethylene | —NH— | m-CF$_3$-phenyl | o-CN | methyl | O | O | 2 | b | 131–133° |
| 40 | ethylene | —NH— | o-MeO-phenyl | o-CN | methyl | O | O | 2 | b | 126–128° |
| 41 | ethylene | —NH— | m-MeO-phenyl | o-CN | methyl | O | O | 2 | b | 115–117° |
| 42 | ethylene | —NH— | o,o-di-Me-phenyl | o-CN | methyl | O | O | 2 | b | 160–163° |
| 43 | ethylene | —NH— | p-CN-phenyl | o-CN | methyl | O | O | 2 | b | 124–126° |
| 44 | ethylene | —NH— | p-tolyl | o-CN | methyl | O | O | 2 | b | 127–129° |
| 45 | ethylene | —NH— | cyclohexyl | o-Br | methyl | O | O | 2 | b | 113–116° |
| 46 | ethylene | —NH— | cyclohexyl | o-CN | methyl | O | O | 2 | b | 131–133° |
| 47 | ethylene | —NH— | phenyl | o-CN | phenyl | O | O | 2 | b | 113–115° |
| 48 | ethylene | bond | p-MeO-phenyl | o-Br | methyl | O | O | 2 | b | 109–111° |

The following compounds of formula I may also be obtained in a manner analogous to Example 1.

-continued

| Example No. | A | X | R | R₁[a] | R₂ | Y | Z | n | M.P. |
|---|---|---|---|---|---|---|---|---|---|
| 49 | ethylene | bond | p-MeO-phenyl | o-CN | methyl | O | O | 2 | b 129–132° |
| 50 | ethylene | —NH— | p-H₂NCO-phenyl | o-CN | methyl | O | O | 2 | b 142–144° |
| 51 | ethylene | bond | p-H₂N-phenyl | o-CN | methyl | O | O | 2 | b 85–87° |
| 52 | ethylene | —NH— | p-OH-phenyl | o-CN | cyclopropylmethyl | O | O | 2 | b 91–93° |
| 53 | ethylene | —NH— | p-OH-phenyl | o-Br | cyclopropylmethyl | O | O | 2 | b 110–112° |
| 54 | ethylene | bond | p-OH-benzyl | o-CN | cyclopropylmethyl | O | O | 2 | b 88–90° |
| 55 | ethylene | bond | p-OH-benzyl | o-Br | cyclopropylmethyl | O | O | 2 | b 82–85° |
| 56 | ethylene | —NH— | m-OH-phenyl | o-CN | cyclopropylmethyl | O | O | 2 | b 68–70° |
| 57 | ethylene | —NH— | o-OH-phenyl | o-CN | cyclopropylmethyl | O | O | 2 | b 110–112° |
| 58 | ethylene | —NH— | m-,p-di-OH-phenyl | o-CN | cyclopropylmethyl | O | O | 2 | |
| 59 | ethylene | —NH— | m-OH-phenyl | o-Br | cyclopropylmethyl | O | O | 2 | |
| 60 | ethylene | —NH— | o-OH-phenyl | o-Br | cyclopropylmethyl | O | O | 2 | |
| 61 | ethylene | —NH— | m-,p-di-OH-phenyl | o-Br | cyclopropylmethyl | O | O | 2 | |
| 62 | ethylene | —NH— | p-tolyl | o-Br | methyl | O | O | 2 | b 126–129° |
| 63 | ethylene | —NH— | p-CN-phenyl | o-Br | methyl | O | O | 2 | b 109–111° |
| 64 | ethylene | —NH— | o,o-di-Me-phenyl | o-Br | methyl | O | O | 2 | b 163–165° |
| 65 | ethylene | —NH— | m-MeO-phenyl | o-Br | methyl | O | O | 2 | b 120–122° |
| 66 | ethylene | —NH— | o-CF₃-phenyl | o-Br | methyl | O | O | 2 | b 108–111° |
| 67 | ethylene | —NH— | m-CF₃-phenyl | o-Br | methyl | O | O | 2 | b 118–120° |
| 68 | ethylene | —NH— | p-H₂NCO-phenyl | o-CN | cyclopropylmethyl | O | O | 2 | b 156–159° |
| 69 | ethylene | —NH— | p-tolyl | o-CN | cyclopropylmethyl | O | O | 2 | b 125–127° |
| 70 | ethylene | —NH— | p-OH-phenyl | o-CN | isopropyl | O | O | 2 | b 103–105° |
| 71 | ethylene | —NH— | phenyl | o-CN | isopropyl | O | O | 2 | b 105–107° |
| 72 | ethylene | —NH— | p-hydroxymethyl-phenyl | o-CN | cyclopropylmethyl | O | O | 2 | b 113–116° |
| 73 | ethylene | —NH— | m-hydroxyphenyl | o-CN | methyl | O | O | 2 | b 160–162° |
| 74 | ethylene | —NH— | p-hydroxyphenyl | o-CN | phenyl | O | O | 2 | b 123–125° |
| 75 | ethylene | —NH— | p-hydroxyphenyl | o-CN | isobutyl | O | O | 2 | b 180–182° |
| 76 | ethylene | —NH— | (p-hydroxy,m-hydroxymethyl)-phenyl | o-CN | cyclopropylmethyl | O | O | 2 | |
| 77 | ethylene | —NH— | (m-cyano,p-hydroxy)phenyl | o-CN | cyclopropylmethyl | O | O | 2 | |
| 78 | ethylene | —NH— | (p-cyano,m-hydroxy)phenyl | o-CN | cyclopropylmethyl | O | O | 2 | |
| 79 | ethylene | —NH— | (m-carbamoyl,p-hydroxy)phenyl | o-CN | cyclopropylmethyl | O | O | 2 | |
| 80 | ethylene | —NH— | (p-carbamoyl,m-hydroxy)phenyl | o-CN | cyclopropylmethyl | O | O | 2 | |
| 81 | ethylene | —NH— | p-chlorophenyl | o-CN | cyclopropylmethyl | O | O | 2 | b 133–136° |
| 82 | —C(CH₃)₂CH₂— | —NH— | p-hydroxyphenyl | o-CN | cyclopropylmethyl | O | O | 2 | | b = in free base form
hml = in hydrogen maleate salt form
hmo = in hydrogen malonate salt form
ox = in bis[base]oxalate salt form
Me = methyl
MeO = methoxy
M.P. = melting point

[a] o- resp. m- = in the position on the phenyl ring ortho or meta, respectively, to the 3-aminopropoxy side chain.
[b] The intermediate 2-benzyloxy-5-(2-methoxyethoxy)benzamide (M.P. 113–115°) is obtained by hydrolyzing 2-benzyloxy-5-(2-methoxyethoxy)benzonitrile (M.P. 50–51°) with potassium hydroxyde in tert-butanol at reflux temperature.
[c] The intermediate 2-benzyloxy-5-(2-methoxyethoxy)-1-pyrrolyl-benzene (oil) is obtained by reacting 2-benzyloxy-5-(2-methoxyethoxy)benzamide (see b) under the conditions of a Hofmann degradation and further reacting the resultant 2-benzyloxy-5-(2-methoxyethoxy)-1-amino-benzene (oil) with 2,5-diethoxytetrahydrofuran at reflux temperature in dioxane/acetic acid.
[d] The intermediate 2-allyl-4-(2-methoxyethoxy)phenol (oil) is obtained by reacting 4-(2-methoxyethoxy)phenol (M.P. 98–99°) with allyl bromide in acetone/potassium carbonate solution at reflux temperature for 24 hours and heating the resultant 1-allyloxy-4-(2-methoxyethoxy)benzene (oil) in 1,2-dichlorbenzene at 180° for 18 hours.
[e] The intermediate 1-acetamido-2-benzyloxy-4-(2-methoxyethoxy)benzene (M.P. 67–69°) is obtained by acetylating 2-benzyloxy-5-(2-methoxyethoxy)-1-amino-benzene (see c) in ether at reflux temperature.
[f] The intermediate 1-benzyloxy-2-methoxycarbonylamino-4-(2-methoxyethoxy)benzene (oil) is obtained by reacting 2-benzyloxy-5-(2-methoxyethoxy)benzamide (see b) with sodium methylate and bromine at 55° in methanol.
[g] The intermediate 5-benzyloxy-2-(2-methoxyethoxy)benzonitrile (oil) is obtained by reacting at 0° 4-benzyloxyphenol in methanol with bromine dissolved in chloroform, further reacting the resultant 4-benzyloxy-2-bromo-phenol (oil) with (2-chloroethyl)-(methyl)ether in aqueous sodium hydroxide at reflux temperature and further reacting the resultant 1-benzyloxy-3-bromo-4-(2-methoxyethoxy)benzene (oil) in dimethylformamide with cuprous cyanide at reflux temperature for 5 hours.
[h] The intermediate 1-acetamido-5-benzyloxy-2-(2-methoxyethoxy)bezene (oil) is obtained by hydrolyzing 3-benzyloxy-6-(2-methoxyethoxy)benzonitrile (see g) in potassium butanolate at reflux temperature, further reacting the resultant 3-benzyloxy-6-(2-methoxyethoxy)benzamide (M.P. 137–139°) with sodium methylate and bromine at 55°, further reacting the resultant 1-benzyloxy-3-methoxy-carbonylamino-4-[2-methoxyethoxy)benzene (oil) with sodium hydroxide in water/dimethyl sulfoxide at 70° and acetylating the resultant 3-benzyloxy-6-(2-methoxyethoxy)1-amino-benzene (oil) in ether at reflux temperature.
[i] The intermediate 1-acetyl-2-benzyloxy-5-(2-methoxyethoxy)benzene (oil) is obtained by reacting 1-acetyl-2,5-dihydroxybenzene at reflux temperature with a mixture of potassium carbonate, acetone and benzyl bromide, and further reacting the resultant 3-acetyl-4-benzyloxyphenol (oil) with (2-chloroethyl)-(methyl)ether in aqueous sodium hydroxide at 100°.

| Example | A | X | R | R₁(a) | R₂ | Y | Z | n |
|---|---|---|---|---|---|---|---|---|
| A | trimethylene | bond | —CH₂CH=CH₂ | m-isopropyl | H | O | bond | 1 |
| B | —C(CH₃)₂—(CH₂)₂— | —NH— | —CH₂CH₂CH=CH—CH₃ | m-F | —CH₂CH₂CH=CH₂ | S | bond | 3 |
| C | trimethylene | —NH— | cyclopentyl | o-cyclopropyl | cyclopentyl | S | O | 3 |
| D | trimethylene | —NH— | cyclopropylmethyl | o-I | cycloheptylbutyl | O | bond | 2 |
| E | —CH(CH₃)—(CH₂)₂— | —NH— | o-fluorophenyl | m-cyclohexyl | p-tert-butylphenyl | S | bond | 1 |
| F | trimethylene | —NH— | —CH(CH₃)(CH₂)₂—(phenyl, R = —OCH₂OCH₂CH₃) | m-CF₃ | m-fluorophenylpentyl | O | bond | 3 |
| G | trimethylene | bond | —CH₂CH₂CHCH₃—cyclohexyl | o-O(CH₂)₃CH=CH₂ | —CH₂CH₂CH=CH—(3,4-diethoxyphenyl) | S | bond | 1 |
| H | —(CH₂)₂C(CH₃)₂— | bond | —CH=CH(CH₂)₃—(m-bromophenyl) | m-COCH₂CH₃ | (2,3-diethoxy-5-ethylphenyl)-OCH₂CH₃ | O | O | 3 |
| I | pentamethylene | bond | —(CH₂)₃—(3,4-diethoxy-5-ethylphenyl) | m-NHCHO | H | S | O | 3 |
| J | trimethylene | bond | —CH(CH₃)(CH₂)₂—(m-NHCOCH₃-phenyl) | m-isopropoxy | H | O | O | 2 |

-continued

| Example | A | X | R | $R_1^{(a)}$ | $R_2$ | Y | Z | n |
|---|---|---|---|---|---|---|---|---|
| K | trimethylene | bond | —CH(CH$_3$)CH— (3-methoxy-4-hydroxyphenyl) | o-ethylthio | H | S | bond | 3 |
| L | trimethylene | bond | m-fluoro-p-hydroxyphenyl | m-NO$_2$ | o-isopropoxyphenyl | S | O | 2 |
| M | trimethylene | bond | —CH$_2$CH(CH$_3$)CH$_2$—CH$_2$— (2,6-dimethyl-4-isopropoxyphenyl) | O—NH$_2$ | —CH$_2$CH=CHCH$_2$— (phenyl-NHCOCH(CH$_3$)$_2$) | S | O | 2 |

$^{(a)}$o- resp. m- = in the position on the phenyl ring ortho or meta, respectively, to the 3-aminopropoxy side chain.

The following derivatives, esters of the compounds of formula I (which are compounds of formula E) may be obtained by appropriately esterifying the 2 position of the 3-aminopropoxy side chain in the corresponding compounds of formula I (the other substituents are as for the corresponding compound of formula I):

| Ex. No. | Corresponding compound of formula I (Example No.) | $R_e$ (formula E) |
| --- | --- | --- |
| 1-E | 5 | n-nonyl |
| 2-E | 5 | 3-ethylbenzyl |

In a first group of compounds X is a bond,
In a 2nd group of compounds X is imino,
In a 3rd group of compounds Y is an oxygen atom,
In a 4th group of compounds Y is a sulfur atom,
In a 5th group of compounds Z is an oxygen atom,
In a 6th group of compounds Z is a bond,
In a 7th group of compounds n is 2,
In a 8th group of compounds R is alkyl,
In a 9th group of compounds R is alkenyl.
In a 10th group of compounds R is cycloalkyl or cycloalkylalkyl,
In a 11th group of compounds R is cycloalkylalkyl,
In a 12th group of compounds R is optionally substituted aryl,
In a 13th group of compounds R is optionally substituted aralkyl,
In a 14th group of compounds R is optionally substituted aralkenyl,
In a 15th group of compounds $R_1$ is hydrogen.
In a 16th group of compounds $R_1$ is a substituent.
In a 17th group of compounds $R_1$ is cyano,
In a 18th group of compounds $R_1$ is in the position ortho to the 3-aminopropoxy side chain,
In a 19th group of compounds $R_1$ is in the position meta to the 3-aminopropoxy side chain,
In a 20th group of compounds $R_2$ is hydrogen,
In a 21th group of compounds $R_2$ is other than hydrogen,
In a 22nd group of compounds $R_2$ is alkyl or alkenyl,
In a 23rd group of compounds $R_2$ is cycloalkyl or cycloalkylalkyl,
In a 24th group of compounds $R_2$ is cycloalkylalkyl.
In a 25th group of compounds $R_2$ is optionally substituted aryl.
In a 26th group of compounds $R_2$ is optionally substituted aralkyl.
In a 27th group of compounds $R_2$ is optionally substituted aralkenyl.
In a 28th group of compounds A is ethylene.
In a 29th group of compounds $R_1$ is hydrogen or cyano,
$R_2$ is cycloalkylalkyl and R is optionally substituted aryl or aralkyl.

The compounds of the invention are useful because they possess pharmacological activity in animals.

In particular, the compounds possess β-adrenoceptor blocking activity, as indicated by standard tests. For example, in the spontaneously beating guinea pig atrium (A. Bertholet et al., Postgrad. Med. J. 57, Suppl. 1 [1981], 9–17) they inhibit the positive chronotropic isoprenaline effect at bath concentrations of from about $10^{-8}$M to about $10^{-6}$M and in the spinal cat (B. Ablad et al., Acta Pharmacol. 25, Suppl. 2 [1967], 9) at a dosage of from about 0.02 mg/kg to about 1 mg/kg i.v.

Thus, in the two tests above, the following compounds exhibit effective β-adrenoceptor blocking activity at the dose indicated below:

| Exampl. No. | Guinea pig atrium test Effective dose [molar concentration] [M] | Spinal cat test Effective dose [mg/kg i.v.] |
| --- | --- | --- |
| 1 | $2 \times 10^{-8}$ | 0.02 |
| 2 | $4 \times 10^{-8}$ | 0.02 |
| 8 | $5 \times 10^{-8}$ | 0.1 |
| 17 | $2 \times 10^{-7}$ | 0.2 |
| 50 | $3 \times 10^{-7}$ | 0.02 |
| 52 | $2 \times 10^{-8}$ | 0.004 |
| Propranolol | $3 \times 10^{-9}$ | 0.01 |

The compounds are therefore useful as β-adrenoceptor blocking agents, e.g. for the prophylaxis and therapy of coronary diseases, such as angina pectorts, conditions which are associated with sympathetic over-stimulation, e.g. nervous heart complaints, myocardial infarction, hypertension, for the intermediate treatment of migraine and for the treatment of glaucoma and thyreotoxtcosis. In view of their antiarrhythmic effect, they are useful as antiarrhythmics for the treatment of disturbances in the heart rhythm, such as supraventricular tachycardia.

For these uses, the dose will, of course, vary according to the substance used, the mode of administration and the desired treatment. In general, however, satisfactory results are obtained with a daily dosage of about 0.1 mg to about 10 mg per kg body weight; administration may be effected in 2 to 4 divided doses, or in sustained release form. For the larger mammal, the total daily dosage is from about 10 mg to about 500 mg, suitable forms for oral administration generally contain from about 2.5 mg to about 250 mg of the compounds together with solid or liquid carriers and/or diluents.

An example of a dosage range is from abut 20 mg to about 200 mg, preferably from about 50 mg to about 100 mg.

The compounds have more marked and wider spread beneficial pharmacological properties than could be expected for compounds having this type of structure. In particular, their activity is more cardioselective than could be expected from similar known compounds. This cardioselectivity can be demonstrated in vitro by the use of isolated tissues of the guinea-pig, in accordance with standard procedures. Thus, left ventricular and lung membranes of a guinea-pig can be prepared according to standard pharmacological procedures (G. Engel et al., Triangle 19 [1980]69–76; G. Engel, Postgrad.Med.J. 57 [1981], Suppl. 1, 77–83) and made to react with an exogenously added radio-active β-ligand such as 3-[$^{125}$I]iodocyanopindoloi (I-CYP) to determine affinity of the test compound to $\beta_1$ and $\beta_2$ adrenoceptors.

Thus, for the following compounds, the affinity to $\beta_1$-adrenoceptors is greater than the affinity to $\beta_2$-adrenoceptors by the factor indicated below:

| Exampl. No. | Cardioselectivity ratio |
| --- | --- |
| 1 | 2800 |
| 2 | 740 |
| 8 | 1400 |
| 17 | 1200 |
| 50 | 5100 |
| 52 | 3000 |

| Exampl. No. | Cardioselectivity ratio |
| --- | --- |
| Propranolol | 0.9 |

Guinea pig lung and left ventricular membranes may e.g. be prepared as follows:

Adult guinea pigs (350–550 g) are killed by decapitation. The heart and lung are perfused with Tris saline buffer (Tris-HCl 10 mM, pH=7.5, NaCl 0.154M ), removed and freed from connective tissues and trachea. The lung membranes are prepared as described by Kleinstein, J. and Glossmann H., Naunyn-Schmiedeberg's Arch. Pharmacol. 305 [1978], 191–200 with the modification that medium A contains only 20 mM $NaHCO_3$. The final pellet is suspended in 10 ml 20 mM $NaHCO_3$ and stored in liquid nitrogen. The preparation of the left ventricle membranes follows the procedure published by McNamanra, D. B. et al., J.Biochem. 75 [1974], 795–803 until the step where the 'membrane fraction' is received. These membranes are stored in liquid nitrogen and immediately before use further diluted to the appropriate concentrations as indicated in the text.

The high selectivity of blockade for these compounds is of major importance in the treatment of hypertension where exacerbation of an existing asthmatic condition may be precipitated by currently commercially available compounds.

The compounds also possess a degree of intrinsic sympathomimetic activity, a property which is useful in preventing undue bradycardia and helps reduce the incidence of heart failure in subjects with heart muscle disease.

Of the compounds in optically active form, those in which the carbon atom in the 2-position of the 3-aminopropoxy side chain has the (S)-configuration are pharmacologically more active than the corresponding (R)-enantiomers.

The preferred uses of the compounds are the use against coronary diseases and hypertension.

Preferred are the compounds of Examples 2, 8, 17, 50 and 51, especially of Examples 2, 8 and 52, especially of Examples 2 and 8.

The compounds of the invention in free form or in the form of their pharmaceutically acceptable salts may be administered alone or in suitable dosage forms. The present invention also provides a pharmaceutical composition comprising a compound of the invention in free form or in salt, preferably acid addition salt form in association with a pharmaceutical carrier or diluent. Such forms, e.g. a solution or a tablet, may be produced according to known methods.

We claim:

1. A compound of formula I

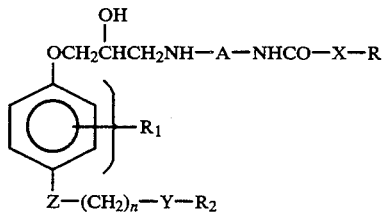

wherein

R is alkyl, alkenyl, cycloalkyl, cycloalkylalkyl or optionally substituted aryl, aralkyl or aralkenyl, $R_1$ is hydrogen, alkyl of 1 to 4 carbon atoms, alkoxy of 1 to 4 carbon atoms, alkylthio of 1 to 4 carbon atoms, cycloalkyl of 3 to 7 carbon atoms, halogen of atomic number of from 9 to 53, trifluoromethyl, pyrrol-1-yl, cyano, carbamoyl, alkenyl of 2 to 5 carbon atom, alkenyloxy of 3 to 5 carbon atoms wherein the double bond is not attached to the carbon atom adjacent to the oxygen atom, alkanoyl of 2 to 5 carbon atoms, nitro, amino, alkanoylamino of 1 to 5 carbon atoms or alkoxycarbonylamino of 1 to 4 carbon atoms in the alkoxy moiety thereof, $R_2$ is hydrogen or has the significance indicated above for R, A is alkylene, X is a bond Y is an oxygen or a sulfur atom and either Z is an oxygen atom and n is 2 or 3 or Z is a bond and n is 1, 2 or 3, with the provisos that when $R_2$ is cycloalkylalkyl and R is alkyl then $R_1$ is other than hydrogen, and when $R_2$ is hydrogen, then Z is an oxygen atom, or physiologically acceptable hydrolyzable derivative thereof having the hydroxy group in the 2 position of the 3-aminopropoxy side chain in esterified form, or a pharmaceutically acceptable salt form thereof.

2. A compound of claim 1 of formula Ia,

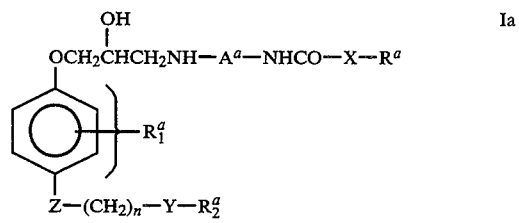

wherein X, Y, Z and n are as defined above and $R^a$ is alkyl of 1 to 4 carbon atoms, alkenyl of 3 to 5 carbon atoms wherein the double bond is not attached to the carbon atom adjacent to X, cycloalkyl of 5 to 7 carbon atoms, cycloalkylalkyl of 3 to 7 carbon atoms in the cycloalkyl moiety, and of 1 to 4 carbon atoms in the alkyl moiety thereof, or phenyl, phenylalkyl of 7 to 10 carbon atoms or phenylalkenyl of 8 to 11 carbon atoms wherein the double bond is not attached to the carbon atom adjacent to X, the last three substituents optionally being:

i) monosubstituted in the phenyl ring by alkyl of 1 to 4 carbon atoms, alkoxy of 1 to 4 carbon atoms, halogen of atomic number of from 9 to 35, hydroxy, cyano, trifluoromethyl, hydroxymethyl, carbamoyl, alkoxyalkoxy of 1 to 4 carbon atoms in each of the alkoxy moieties thereof, amino or alkanoylamino of 1 to 5 carbon atoms, or ii) independently disubstituted in the phenyl ring by alkyl of 1 to 4 carbon atoms, hydroxymethyl, carbamoyl, cyano, alkoxy of 1 to 4 carbon atoms, halogen of atomic number of from 9 to 35 or hydroxy, or iii) independently trisubstituted in the phenyl ring by alkyl of 1 to 4 carbon atoms or alkoxy of 1 to 4 carbon atoms, $R_1{}^a$ is hydrogen, alkyl of 1 to 4 carbon atoms, alkoxy of 1 to 4 carbon atoms, alkylthio of 1 to 4 carbon atoms, cycloalkyl of 3 to 7 carbon atoms, halogen of atomic number of from 9 to trifluoromethyl, pyrrol-1-yl, cyano, carbamoyl, alkenyl of 2 to 5 carbon atoms, alkenyloxy of 3 to 5 carbon atoms wherein the double bond is not attached to the carbon atom adjacent to the oxygen atom, alkanoyl of 2 to 5 carbon atoms, nitro, amino, alkanoylamino of 1 to 5 carbon atoms or alkoxycarbonylamino of 1 to 4 carbon atoms in the alkoxy moiety thereof, $R_2{}^a$ is hydrogen, alkyl of 1 to 5 carbon atoms, alkenyl of 3 to 5 carbon atoms wherein the double bond is not attached to the carbon atom adjacent to Y, cycloalkyl of 5 to 7 carbon atoms, cycloalkylalkyl of 3 to 7 carbon atoms in the cycloalkyl moiety and of 1 to 4 carbon atoms in the alkyl moiety thereof, or phenyl, phenylalkyl of 7 to 10 carbon atoms or phenylalkenyl of 8 to 11 carbon atoms wherein the double bond is not attached to the carbon atom adjacent to Y, the last three substituents optionally being mono- or independently di- or independently trisubstituted in the phenyl ring by alkyl of 1 to 4 carbon atoms, alkoxy of 1 to 4 carbon atoms or halogen of atomic number of from 9 to 35 and $A^a$ is alkylene of 2 to 5 carbon atoms, with the provisos that when $R_2{}^a$ is cycloalkylalkyl of 3 to 7 carbon atoms in the cycloalkyl moiety and of 1 to 4 carbon atoms in the alkyl moiety thereof, $R^a$ is alkyl of 1 to 4 carbon atoms and X is a bond, then $R_1{}^a$ is other than halogen, and when $R_2{}^a$ is hydrogen, Z is an oxygen atom, or a physiologically acceptable hydrolyzable derivative thereof having the hydroxy group in the 2 position of the 3-aminopropoxy side chain in esterified form, or a pharmaceutically acceptable salt form thereof.

3. A process for the production of a compound of claim 1, which includes the step of appropriately 3-amino-2-oxypropylating a corresponding compound of formula IV,

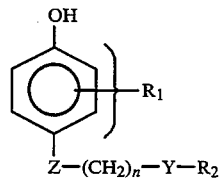

wherein $R_1$, $R_2$, Z, Y and n are as defined in claim 1, or a precursor form thereof.

4. A process according to claim 3 for the production of a compound of claim 1, which comprises reacting a corresponding compound of formula II,

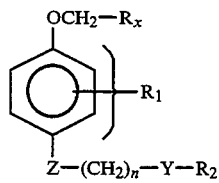

wherein $R_1$, $R_2$, Z, Y and n are as defined in claim 1 and $R_x$ is a group capable of reacting with a primary amine to give a 2-amino-1-hydroxyethyl group, with a corresponding compound of formula III,

wherein A, X and R are as defined in claim 1 and, where required, appropriately esterifying the 2 position of the 3-aminopropoxy side chain in the resultant compound of formula I, and recovering the resultant compound in free form or in salt form.

5. A pharmaceutical composition comprising a compound of claim 1 in association with a pharmaceutical carrier or diluent.

6. A method of treating coronary diseases, conditions associated with sympathetic overstimulation, myocardial infarction, hypertension, migraine, glaucoma, thyreotoxicosis or heart rhythm disorders, which comprises administering to an animal in need of such treatment a therapeutically effective amount of a compound of claim 1.

7. A method of effecting $\beta$-adrenoceptor blockade, which comprises administering to an animal in need of such treatment a therapeutically effective amount of a compound of claim 1.

* * * * *